United States Patent
Boros et al.

(10) Patent No.: US 9,803,887 B2
(45) Date of Patent: Oct. 31, 2017

(54) CATHODIC CORROSION AND DRY FIRE PROTECTION APPARATUS AND METHODS FOR ELECTRIC WATER HEATERS

(71) Applicant: Rheem Manufacturing Company, Atlanta, GA (US)

(72) Inventors: Jozef Boros, Montgomery, AL (US); Raheel A. Chaudhry, Montgomery, AL (US); Yan Hong, Montgomery, AL (US); Troy E. Trant, Montgomery, AL (US)

(73) Assignee: RHEEM MANUFACTURING COMPANY, Atlanta, GA (US)

( * ) Notice: Subject to any disclaimer, the term of this patent is extended or adjusted under 35 U.S.C. 154(b) by 554 days.

(21) Appl. No.: 14/305,581

(22) Filed: Jun. 16, 2014

(65) Prior Publication Data

US 2014/0376899 A1    Dec. 25, 2014

Related U.S. Application Data

(60) Provisional application No. 61/838,749, filed on Jun. 24, 2013.

(51) Int. Cl.
*F24H 1/20*    (2006.01)
*F24H 9/00*    (2006.01)
(Continued)

(52) U.S. Cl.
CPC .......... *F24H 9/0047* (2013.01); *C23F 13/04* (2013.01); *C23F 13/22* (2013.01); *F24H 9/2021* (2013.01);
(Continued)

(58) Field of Classification Search
CPC .......... F24H 9/0047; F24H 9/122; F24H 9/14; F24H 9/20; F24H 9/007; F24H 9/0005; F24H 9/0021; F24H 9/2014; F24H 9/2021; F24H 1/20; F24H 1/201; F24H 1/202; F24H 1/203; F24H 1/22; F24H 1/48; F24H 1/46; F24H 1/50; C23F 13/00; C23F 13/02; C23F 13/04; C23F 13/06; C23F 13/08;
(Continued)

(56) References Cited

U.S. PATENT DOCUMENTS

| | | | |
|---|---|---|---|
| 3,037,920 A | 6/1962 | Vixler | |
| 3,769,521 A | 10/1973 | Caldwell et al. | |
| 4,087,742 A * | 5/1978 | Khoo | C23F 13/02 204/196.07 |
| 4,147,608 A | 4/1979 | Stevens | |
| 4,219,807 A | 8/1980 | Speck et al. | |
| 4,255,647 A | 3/1981 | Rickert et al. | |
| 4,306,189 A | 12/1981 | Nozaki | |
| 4,972,066 A * | 11/1990 | Houle | C23F 13/02 204/196.05 |

(Continued)

FOREIGN PATENT DOCUMENTS

WO    WO 93 04217    3/1993
WO    WO 2009 029287    3/2009

*Primary Examiner* — Shawntina Fuqua
(74) *Attorney, Agent, or Firm* — King & Spalding LLP

(57) ABSTRACT

The metal tank portion of an electric water heater is protected against corrosion utilizing a corrosion protection system that detects a voltage potential between the sheath portion of a tank water-immersed electric heating element and the tank. In one embodiment of the corrosion protection system the sensed sheath/tank potential is utilized to enable a user of the water heater to accurately gauge the necessity of replacing a sacrificial anode extending into the tank. In another corrosion protection system, the sensed sheath/tank potential is utilized to provide impressed current cathodic protection of the tank and also to prevent dry firing of the electric water heater.

14 Claims, 4 Drawing Sheets

(51) Int. Cl.
  *F24H 9/20* (2006.01)
  *C23F 13/04* (2006.01)
  *C23F 13/22* (2006.01)
  *G01N 17/02* (2006.01)
  *G05B 23/02* (2006.01)

(52) U.S. Cl.
  CPC ......... *G01N 17/02* (2013.01); *G05B 23/0235* (2013.01); *C23F 2213/21* (2013.01); *F24H 1/202* (2013.01)

(58) Field of Classification Search
  CPC .......... C23F 13/14; C23F 13/20; C23F 13/22; C23F 2213/30; C23F 2213/31; C23F 2213/21; G01N 17/02
  See application file for complete search history.

(56) References Cited

U.S. PATENT DOCUMENTS

| | | |
|---|---|---|
| 6,611,133 B2 | 8/2003 | Kean et al. |
| 6,903,540 B2 | 6/2005 | Kean et al. |
| 6,932,891 B2 | 8/2005 | Wigg et al. |
| 7,468,321 B2 | 12/2008 | Ching et al. |
| 7,951,286 B2 | 5/2011 | Dwars et al. |
| 8,068,727 B2 * | 11/2011 | Phillips ................. F24H 9/0047 392/441 |
| 2003/0189435 A1 | 10/2003 | Yunovich et al. |
| 2004/0051514 A1 | 3/2004 | Kean et al. |
| 2005/0006251 A1 | 1/2005 | Thomas, III et al. |
| 2009/0295368 A1 | 12/2009 | Doogue et al. |

\* cited by examiner

CATHODIC CORROSION AND DRY FIRE PROTECTION APPARATUS AND METHODS FOR ELECTRIC WATER HEATERS

CROSS-REFERENCE TO RELATED APPLICATION

The present application claims the benefit of the filing date of provisional U.S. patent application Ser. No. 61/838,749 filed Jun. 24, 2013. The entire disclosure of the provisional application is hereby incorporated herein by this reference.

BACKGROUND OF THE INVENTION

In a typical electric water heater, or in other types of electric liquid heating apparatus, the liquid to be heated is disposed in a vessel into which a resistance-type submersible electric heating element projects and may be selectively energized to heat the liquid to a predetermined temperature. As commonly manufactured, the vessel is of a ferrous metal material, such as steel, which is lined with a protective ceramic or other material to inhibit corrosion of the metal which can lead to leakage of the vessel. Corrosion is essentially an electrochemical phenomenon, and cathodic protection is a commonly used method of combating it.

The most common techniques for providing such cathodic protection for the liquid-containing vessels or tanks of electric liquid heating apparatus are (1) utilizing an erodable sacrificial anode in the vessel, and (2) using an impressed current cathodic protection (ICCP) anode in the vessel. The sacrificial anode technique has the advantages of low cost, continuous protection without any limitations such as power outage, software malfunction, etc. However, it has a limited life, and must be inspected periodically to verify that it has not dissolved to an extent rendering it incapable of carrying out its cathodic protection function. The ICCP anode protection technique provides several advantages over the sacrificial anode approach to cathodic corrosion protection, such as being capable of being precisely controllable with respect to its potential and current outputs, and having potentially unlimited operational life. However, the ICCP anode protection technique has some disadvantages such as requiring an associated control system and being more complex and costly than a sacrificial anode system.

As can be seen from the foregoing, it would be desirable to provide an electric liquid heating apparatus having incorporated therein improved cathodic corrosion protection apparatus, based on either a sacrificial anode approach or an impressed corrosion inhibiting voltage approach. It is to this goal that the present invention is primarily directed.

DETAILED DESCRIPTION

Figure 1:
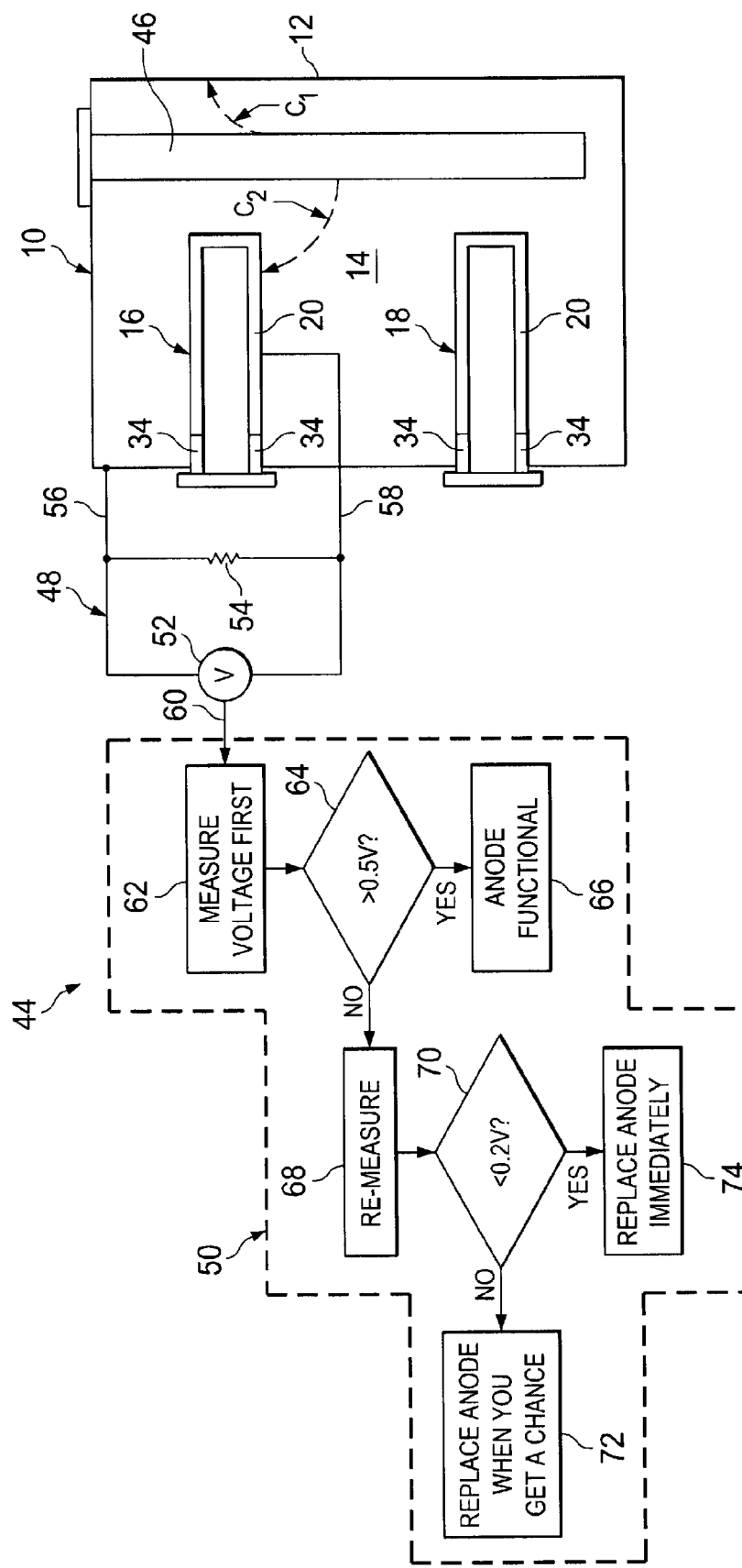
FIG. 1 is a schematic diagram of an electric water heater incorporating therein tank corrosion protection apparatus embodying principles of the present invention and including a sacrificial anode and a specially designed electric resistance type immersion heating element and associated control apparatus, having the illustrated control steps, for monitoring the depletion of the sacrificial anode.

Referring initially to FIG. 1, in a first representative embodiment thereof the present invention provides an electric liquid heating apparatus which is illustratively an electric water heater 10, but could alternately be another type of electric liquid heating apparatus, such as an electric boiler, without departing from principles of the present invention. The electric water heater 10 has a storage vessel in the form of a ferrous metal tank 12, illustratively of a steel construction, having the usual protective ceramic lining (not shown). As is well known in the water heating art, despite the presence of this protective lining, the metal tank 12 is subject to corrosion as its lining wears away over the operational life and/or the pre-existing defect of the lining of the tank 12. Extending inwardly through the tank wall 12 for heating water 14 in the tank 12 are upper and lower submersible resistance type electric heating elements 16,18 that may be selectively energized to heat the water 14.

Figure 2:
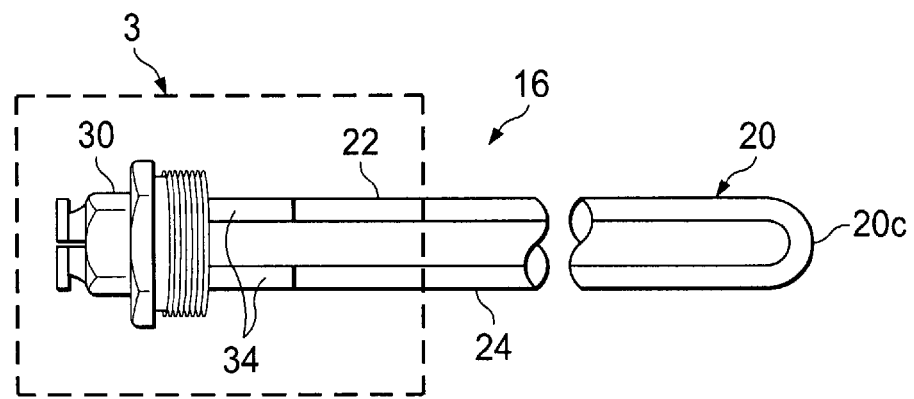
FIG. 2 is a longitudinally foreshortened side elevational view of the specially designed heating element of FIG. 1.
Figure 3:
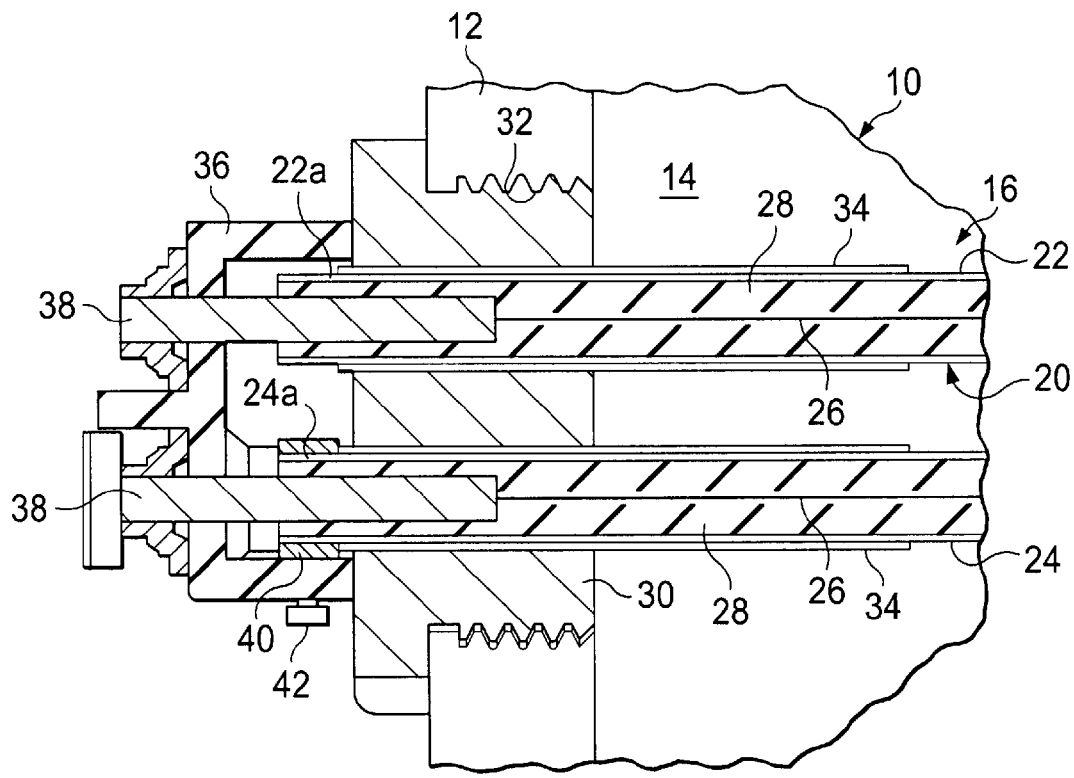
FIG. 3 is an enlarged scale cross-sectional view of the portion of the FIG. 2 heating element within the dashed area "3", with the heating element operatively installed in an electric water heater partially illustrated in phantom in FIG. 3.

Turning now to FIGS. 2 and 3, the upper electric heating element 16 may have a specially designed configuration embodying principles of the present invention. The electric heating element 16 has an elongated, generally U-shaped hollow metal sheath structure 20 with spaced apart parallel legs 22 and 24 having unjoined outer end portions 22a, 24a and inner end portions 22b, 24b joined by a curved sheath section 20c. Representatively, but not by of limitation, the metal material of the sheath structure 20 is titanium. Extending through the interior of the sheath structure 20 is an electric heating filament 26 which is electrically isolated from the sheath structure 20 by suitable insulation material 28 within the sheath structure. The outer sheath ends 22a, 24a extend through corresponding openings in an externally threaded cylindrical metal mounting plug 30 which, with the sheath 20 inserted into the tank interior through an internally threaded mounting hole 32 in the metal tank wall 12, is threaded into the mounting hole 32. As depicted in FIG. 3, the outer sheath ends 22a, 24a are circumscribed by insulating structure illustratively in the form of tubular insulating members 34 (representatively of a plastic material) which extend through the metal mounting plug 30, thereby electrically isolating the sheath 20 from both the mounting plug 30 and the tank 12.

An insulative housing or cover 36, representatively of a plastic material, is suitably secured to the outer side of the metal mounting plug 30 and receives outwardly projecting portions of the outer sheath leg ends 22a, 24a (see FIG. 3). Electrically conductive power connection pins 38 extend inwardly through the housing 36 and into the outer ends 22a, 24a of the sheath 20 wherein the power connection pins 38 are operatively coupled to the opposite ends of the electric heating filament 26.

The power connection pins 38 form a first connection structure, coupled to the electric heating filament 26, through which electrical heating current may be selectively flowed to generate heat used to heat the water 14 in the tank 12. A second connection structure is provided in the form of a metal ring 40 circumscribing the outer sheath leg end 24a and in electrically conductive contact therewith (and electrically isolated from the power connection pins 38), and a metal connector screw 42 is threaded through the housing 36 into electrically conductive contact with the metal ring 40 and thus in electrical communication with the sheath 20. Through the metal connector screw (via an electrical wire connected thereto) an electrical voltage may be impressed on the sheath structure 20, or a voltage potential between the sheath structure 20 and the metal tank 12 may be sensed, for purposes subsequently described herein.

Returning to FIG. 1, in accordance with principles of the present invention, the electric water heater 10 is provided with a specially designed protection apparatus 44 operative to inhibit corrosion of the tank 12. The protection apparatus 44 includes a dissolvable protective anode 46, representatively a magnesium anode, the electrically conductive sheath structure 20 of the upper electric heating element 16, a sensing portion 48, and a control portion 50. Basically, the upper electric heating element sheath 20, the sensing portion 48 and the control portion 50 facilitate the corrosion protection of the tank 12 by sensing and indicating the degree of depletion of the sacrificial anode 46 to enable a user of the water heater 10 to accurately gauge the necessity of replacing the sacrificial anode 46 without removing and inspecting it, and to avoid excessive tank corrosion caused by undetected excessive sacrificial anode depletion.

The sensing portion 48 includes a volt meter 52 connected in parallel with a resistor 54 across electrical leads 56,58 respectively connected to the tank 12 and the sheath 20 of the upper electric heating element 16. For purposes of illustrative clarity, the lead 58 has been schematically depicted in FIG. 1 as being connected to the upper heating element sheath 20 inside the tank 12. However, it will be readily appreciated by those of skill in this particular art that in practice the lead 58 would be connected to the upper heating element metal connector screw 42 outside the tank 12 (see FIG. 3).

During operation of the water heater 10 (with water 14 in the tank 12) electrical current $C_1$ flows from the sacrificial anode 46 to the tank 12, and electrical current $C_2$ flows sequentially from the sacrificial anode 46 to the upper heating element sheath 20, the electrical lead 58, across the resistor 54, and then into the tank 12 via the electrical lead 56. The purpose of the resistor 54 is to limit the magnitude of the electrical current $C_2$ in a manner such that the electrical current flow from the sacrificial anode 46 is predominately the current $C_1$ from the sacrificial anode 46 directly to the tank 12.

With continuing reference to FIG. 1, the volt meter portion 52 of the sensing portion 48 of the protection apparatus 44 detects the voltage across the resistor 54 and outputs a voltage signal 60 indicative of the detected voltage. As the sacrificial anode 46 is progressively depleted, the electrical current $C_2$ progressively diminishes, thereby creating a corresponding reduction in the voltage across the resistor 54. The voltage drop across the resistor is thus indicative of the degree of erosion/depletion of the sacrificial anode 46.

The control portion 50 of the protection apparatus 44, by means of suitable electrical circuitry such as a pre-programmed microprocessor or the like (not shown), utilizes the voltage signal 60 to enable a user of the water heater 10 to accurately gauge the necessity of replacing the sacrificial anode 46 without removing and inspecting it, and to avoid excessive tank corrosion caused by undetected excessive sacrificial anode depletion. The manner of such utilization of the voltage signal 60 entails the following steps depicted in the schematic logic flow diagram portion of FIG. 1 which will now be described.

At step 62 the voltage signal 60 is received by the control portion 50 and measured, and a transfer is made to step 64 at which a query is made as to whether the measured voltage is greater than a predetermined magnitude (representatively 0.5 volts). If it is, a transfer is made to step 66 at which a suitable display is created indicating to the water heater user or technician that the sacrificial anode 46 is functional. If at step 64 it determined that the measured voltage is not greater than the first predetermined magnitude thereof, a transfer is made to step 68 at which the voltage across the resistor 54 is re-measured and a transfer is made to step 70 at which a query is made as to whether the re-measured voltage is less than a second predetermined magnitude (representatively 0.2 volts). If it is not, a transfer is made to step 72 at which a suitable display is created indicating to the water heater user or technician that the sacrificial anode 46 has been depleted to such an extent that it should be replaced soon. If the query answer at step 70 is "yes", a transfer is made to step 74 at which a suitable display is created indicating to the water heater user or technician that the sacrificial anode 46 has been depleted to such an extent that it should be immediately replaced.

Figure 4:
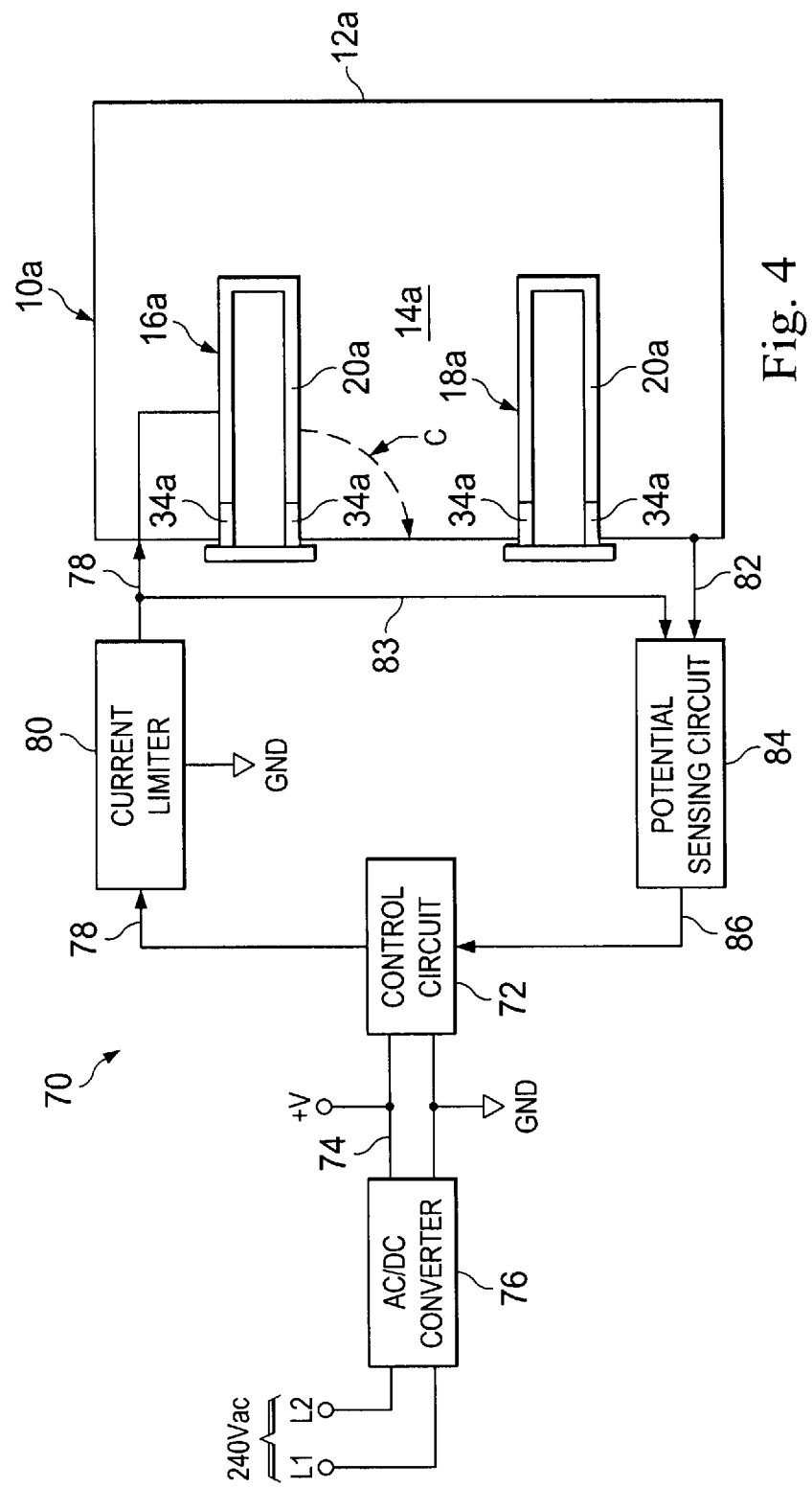
FIG. 4 is a schematic diagram of an alternate electric water heater embodiment incorporating therein combination tank corrosion/dry fire protection apparatus embodying principles of the present invention and including the electric heating element of FIGS. 2 and 3 and associated control apparatus.

Schematically illustrated in FIG. 4 is an alternate embodiment 10a of the previously described electric water heater 10. For ease in comparing the water heater embodiments 10 and 10a, elements in the water heater 10a similar to those in water heater 10 have been given the same reference numerals to which the subscript "a" has been added.

Water heater 10a has a corrodible lined ferrous metal tank 12a into the interior of which upper and lower electric heating elements 16a, 18a project, the heating elements 16a, 18a having the electrically conductive metal sheaths 20a and associated tubular insulating members 34a. Unlike the previously described water heater 10, the water heater 10a is not provided with a sacrificial anode. Instead, a protection apparatus 70 associated with the water heater 10a utilizes the upper heating element sheath 20a to provide the tank 12a of the water heater 10a with impressed current cathodic protection to inhibit corrosion of the tank 12a. The protection apparatus 70 also functions to prevent dry firing of the upper electric heating element 16a.

In addition to the upper heating element electrically conductive sheath 20a, the protection apparatus 70 includes a control portion in the form of a control circuit 72 that receives DC electrical power via electrical lead 74 from an AC/DC convertor 7 fed with 240 volt AC power via lines L1 and L2. An electrical lead 78 has a voltage current limiter 80 therein and is connected to the upper heating element sheath 20a (via the connection screw 42 of the upper heating element 16a as shown in FIG. 2). An electrical lead 82 is connected to the tank 12a and is also coupled to a sensing portion of the protection apparatus 70 in the form of a potential sensing circuit 84. An additional electrical lead 83 connects the electrical lead 78 to the potential sensing circuit 84 to sense potential difference between the tank 12a and the heating element sheath 20a.

Direct electrical current output from the control circuit 72 via electrical lead 78 sequentially flows through the current limiter 80 into the upper heating element sheath 20a, to the tank via current flow C through the tank water 14a, and then into the potential sensing circuit 84 which responsively transmits to the control circuit 72 a signal 86 indicative of the magnitude of the sensed voltage potential between the upper heating element sheath 20*a* and the tank 12*a*.

Figure 5:
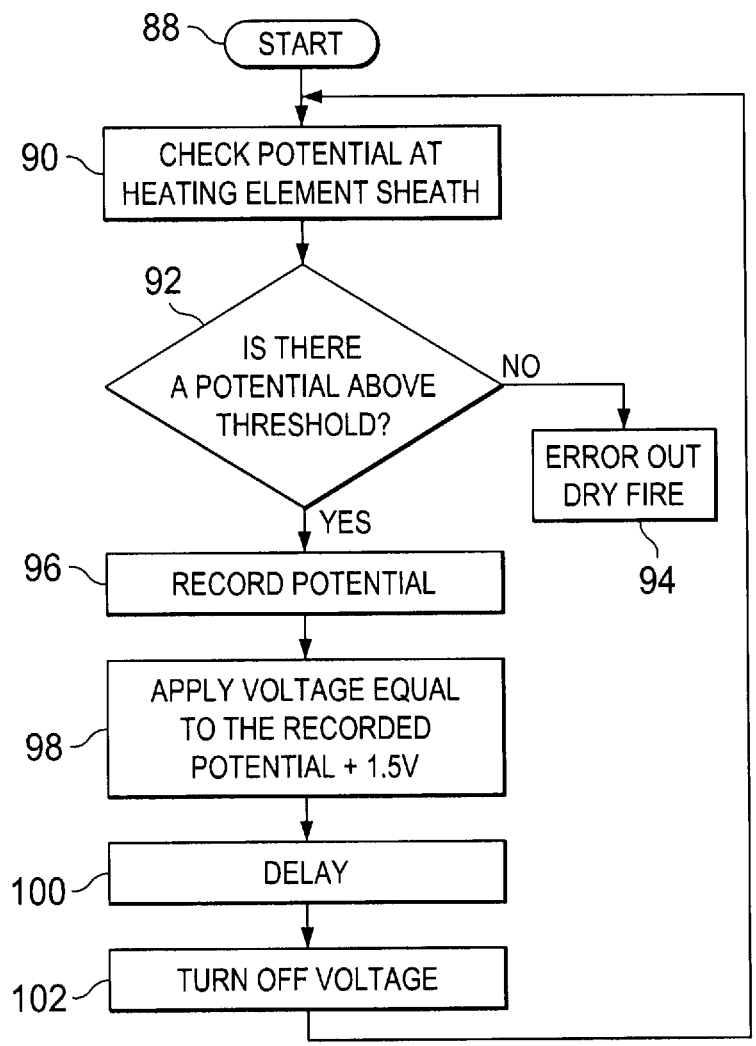
FIG. 5 is a schematic logic flow diagram illustrating the operation of the control apparatus of FIG. 4

FIG. 5 schematically depicts a logic flow chart illustrating the manner in which the control circuit 72 regulates the operation of the protection apparatus 70 to inhibit corrosion of the water heater tank 12*a*. Upon starting the operation of the protection apparatus 70 at step 88, with the operational voltage of the protection apparatus 70 turned off, at step 90 the control circuit 72 checks the voltage potential at the upper heating element sheath 20*a* as represented by the magnitude of the voltage signal 86 received by the control circuit 72 and then makes a query at step 92 as to whether a voltage potential above a predetermined threshold magnitude has been detected. If it has not, a transfer is made to step 94 at which an error signal indicative of a heating element dry fire condition is generated, such error signal being useable to terminate or prevent energization of the upper and lower heating elements 16*a* and 18*a*.

If at step 92 a voltage potential above the predetermined threshold magnitude (which is representatively the "natural" voltage potential between the submerged upper heating element sheath 20*a* and the tank 12*a* without the impression thereon of voltage from the external voltage source), a transfer is made to step 96 at which the detected potential is recorded. Next, at step 98 the protection apparatus supply voltage is turned on and the control circuit 72 outputs a DC voltage equal to the recorded voltage potential plus a predetermined protective voltage magnitude (representatively 1.5 volts DC). Then, at step 100 a predetermined delay period is initiated. After the predetermined delay period expires, a transfer is made to step 102 at which the protection apparatus supply voltage is turned off again and a transfer is made back to step 90 to permit the system to again cycle through the operational steps 90 through 102.

As can be seen from the foregoing, the present invention provides substantial improvements in the cathodic protection of corrodible vessel portions of electric liquid heating apparatus, in both sacrificial anode and impressed current corrosion protection versions thereof. As previously mentioned, although the foregoing description is directed to electric water heater apparatus, the representatively illustrated cathodic protection apparatus and methods of the present invention are not limited to electric water heaters, but may alternatively be used in various other types of electric liquid heating apparatus without departing from principles of the present invention.

Additionally, various modifications can be made to the representatively illustrated liquid heating apparatus without departing from principles of the present invention. For example, and not by way of limitation, various other techniques could be utilized to sense the voltage differential between a heating element sheath and an associated corrodible liquid containment vessel. Moreover, while each of the representative electric water heaters 10 and 10*a* has been shown as having two electric heating elements, a greater or smaller number of electric heating elements could be used without departing from principles of the present invention. Furthermore, where a plurality of electric heating elements are utilized in a given electric heating apparatus vessel, not all of the electric heating elements would have to be configured as shown in FIGS. 2 and 3. Also, other techniques could be utilized to electrically isolate one or more of the depicted electric heating element sheaths from the metal tank.

The foregoing detailed description is to be clearly understood as being given by way of illustration and example only, the spirit and scope of the present invention being limited solely by the appended claims.

What is claimed is:

1. A liquid heating apparatus comprising:
a corrodible vessel;
an electric heating element extending through an interior portion of the corrodible vessel and having an electrically conductive sheath; and
a protection apparatus operative to utilize the electrically conductive sheath to (1) inhibit corrosion of the corrodible vessel and/or (2) prevent dry firing of the electric heating element, the protection apparatus including a sensing portion for sensing the magnitude of a voltage potential between the electrically conductive sheath and the corrodible vessel,
wherein the protection apparatus further includes a control portion coupled to the sensing portion of the protection apparatus and operative to sequentially (1) measure the magnitude of the voltage potential between the electrically conductive sheath and the corrodible vessel in the absence of an impressed voltage potential on the electrically conductive sheath, (2) record the magnitude of the voltage potential if it is above a predetermined value thereof, (3) apply the impressed voltage potential to the electrically conductive sheath equal to the magnitude of the voltage potential that was measured plus a predetermined additional impressed voltage potential magnitude, and (4) terminate the impressed voltage to the electrically conductive sheath.

2. The liquid heating apparatus of claim 1, wherein:
the liquid heating apparatus is an electric water heater.

3. The liquid heating apparatus of claim 1, wherein:
the protection apparatus further includes a sacrificial anode extending through an interior portion of the corrodible vessel.

4. The liquid heating apparatus of claim 3, wherein:
the protection apparatus is operative to utilize the sensed magnitude of the voltage potential between the electrically conductive sheath and the corrodible vessel to detect a degree of depletion of the sacrificial anode.

5. The liquid heating apparatus of claim 3, wherein:
the protection apparatus further includes the control portion coupled to the sensing portion of the protection apparatus and operative to measure the sensed magnitude of the voltage potential between the electrically conductive sheath and the corrodible vessel and:
  (1) if the measured voltage potential magnitude is greater than a first predetermined magnitude, provide an indication that the sacrificial anode is still functional, and
  (2) if the measured voltage potential magnitude is not greater than the first predetermined magnitude, re-measure the sensed magnitude of the voltage potential between the electrically conductive sheath and the corrodible vessel, compare the re-measured voltage potential magnitude to a predetermined second magnitude, and then provide at least one indication of a degree of necessity of replacing the sacrificial anode based on the comparison of the re-measured voltage potential magnitude and the predetermined second magnitude.

6. The liquid heating apparatus of claim 1, wherein:
the sensing portion of the protection apparatus includes a resistor and a voltage measuring device operative to sense the magnitude of the voltage potential between the electrically conductive sheath and the corrodible vessel across the resistor.

7. The liquid heating apparatus of claim 1, wherein:
the protection apparatus includes apparatus for selectively impressing the voltage on the electrically conductive sheath from an external voltage source, and the protection apparatus functions to provide impressed current cathodic protection to the vessel without utilization in the liquid heating apparatus of a separate anode structure for such function.

8. The liquid heating apparatus of claim 1, wherein:
the protection apparatus further includes the control portion coupled to the sensing portion of the protection apparatus and operative to sequentially (1) measure the sensed magnitude of the voltage potential between the electrically conductive sheath and the corrodible vessel, in the absence of an impressed voltage on the electrically conductive sheath, and then (2) output a signal indicative of the dry firing condition of the electric heating element if the measured sensed magnitude of the voltage potential between the electrically conductive sheath and the corrodible vessel is not above a predetermined value thereof.

9. A method of protecting a liquid heating apparatus from operational damage, the liquid heating apparatus having a corrodible vessel adapted to hold liquid to be heated, and an electric heating element extending through an interior portion of the corrodible vessel and having an electrically conductive filament sheath, the method comprising the steps of:
sensing a magnitude of a voltage potential between the electrically conductive sheath and the corrodible vessel; and
utilizing a protection system operative to detect the voltage potential magnitude and use the voltage potential magnitude in (1) inhibiting corrosion of the corrodible vessel and/or (2) preventing dry firing of the electric heating element, wherein the utilizing step includes the further steps of:
sequentially (1) measuring the magnitude of the voltage potential between the electrically conductive sheath and the corrodible vessel in the absence of an impressed voltage on the electrically conductive sheath, (2) recording the magnitude of the voltage potential if it is above a predetermined value thereof, (3) applying the impressed voltage potential to the electrically conductive sheath equal in magnitude to the recorded voltage potential magnitude plus a predetermined additional impressed voltage potential magnitude, and (4) terminating the impressed voltage to the electrically conductive sheath.

10. The method of claim 9 wherein:
the liquid heating apparatus is an electric water heater.

11. The method of claim 9 wherein:
the method further comprises the step of extending a sacrificial anode through an interior portion of the vessel, and
the step of utilizing a protection system includes the step of using the detected voltage potential magnitude to detect the degree of depletion of the sacrificial anode.

12. The method of claim 11 wherein the utilizing step includes the steps of:
utilizing the protection system, if the detected voltage potential magnitude is greater than a first predetermined magnitude, to provide an indication that the sacrificial anode is still functional, and
utilizing the protection system, if the measured voltage potential magnitude is not greater than the first predetermined magnitude, to re-measure the sensed magnitude of the voltage potential between the electrically conductive sheath and the corrodible vessel, comparing the re-measured voltage potential magnitude to a predetermined second magnitude, and then providing at least one indication of the degree of necessity of replacing the sacrificial anode based on the comparison of the re-measured voltage potential magnitude and the predetermined second magnitude.

13. The method of claim 9 further comprising the step of:
selectively impressing a voltage on the electrically conductive sheath from an external voltage source to cause the protection system to provide impressed current cathodic protection to the vessel without utilization in the liquid heating apparatus of a separate anode structure for such function.

14. The method of claim 9 wherein the utilizing step includes the further steps of:
(1) measuring the sensed magnitude of the voltage potential between the electrically conductive sheath and the corrodible vessel, in the absence of an impressed voltage on the electrically conductive sheath, and then (2) outputting a signal indicative of the dry firing condition of the electric heating element if the measured sensed magnitude of the voltage potential between the electrically conductive sheath and the corrodible vessel is not above a predetermined value thereof.

* * * * *